(12) United States Patent
Golubovic-Liakopoulos et al.

(10) Patent No.: US 9,233,080 B2
(45) Date of Patent: Jan. 12, 2016

(54) COMPOSITIONS AND METHODS FOR THE DELIVERY OF AGENTS

(75) Inventors: Nevenka Golubovic-Liakopoulos, Bridgewater, NJ (US); Bhavdeep Shah, Newton, MA (US); Erik Andersen, Lejre (DK)

(73) Assignee: Agigma, Inc., Bridgewater, NJ (US)

( * ) Notice: Subject to any disclaimer, the term of this patent is extended or adjusted under 35 U.S.C. 154(b) by 29 days.

(21) Appl. No.: 12/933,337

(22) PCT Filed: Mar. 26, 2009

(86) PCT No.: PCT/US2009/001910
§ 371 (c)(1),
(2), (4) Date: Nov. 4, 2010

(87) PCT Pub. No.: WO2009/120365
PCT Pub. Date: Oct. 1, 2009

(65) Prior Publication Data
US 2011/0045041 A1    Feb. 24, 2011

Related U.S. Application Data

(60) Provisional application No. 61/040,016, filed on Mar. 27, 2008.

(51) Int. Cl.
| | | |
|---|---|---|
| A61K 8/02 | (2006.01) | |
| A61K 9/00 | (2006.01) | |
| A61K 38/00 | (2006.01) | |
| A61P 17/10 | (2006.01) | |
| A61P 17/16 | (2006.01) | |
| A61P 17/12 | (2006.01) | |
| A61P 17/02 | (2006.01) | |
| A61K 31/375 | (2006.01) | |
| A61K 31/07 | (2006.01) | |
| A61K 31/355 | (2006.01) | |
| A61K 31/122 | (2006.01) | |
| A61K 9/70 | (2006.01) | |
| A61K 8/03 | (2006.01) | |
| A61K 8/65 | (2006.01) | |
| A61K 8/73 | (2006.01) | |
| A61Q 19/00 | (2006.01) | |

(52) U.S. Cl.
CPC .............. *A61K 9/7007* (2013.01); *A61K 8/027* (2013.01); *A61K 8/0208* (2013.01); *A61K 8/03* (2013.01); *A61K 8/65* (2013.01); *A61K 8/731* (2013.01); *A61K 8/733* (2013.01); *A61K 9/0014* (2013.01); *A61K 9/7015* (2013.01); *A61Q 19/00* (2013.01); *A61K 2800/88* (2013.01)

(58) Field of Classification Search
CPC ......... A61K 8/027; A61K 8/65; A61K 8/731; A61K 8/733; A61K 9/7007; A61K 9/7015; A61Q 19/00
USPC .............. 604/46; 424/401, 40; 514/18.6, 474, 514/725
See application file for complete search history.

(56) References Cited

U.S. PATENT DOCUMENTS

| | | | |
|---|---|---|---|
| 3,964,482 A | 6/1976 | Gerstel et al. | 128/260 |
| 5,053,227 A | 10/1991 | Chiang et al. | 424/448 |
| 5,229,130 A | 7/1993 | Sharma et al. | 424/449 |
| 5,693,335 A | 12/1997 | Xia et al. | 424/448 |
| 5,698,155 A | 12/1997 | Grosswald et al. | 264/402 |
| 5,807,570 A | 9/1998 | Chen et al. | 424/449 |
| 5,919,665 A | 7/1999 | Williams et al. | 435/71.1 |
| 6,025,150 A | 2/2000 | Livant et al. | 435/29 |
| 6,352,715 B1 | 3/2002 | Hwang et al. | 424/449 |
| 6,596,296 B1 | 7/2003 | Nelson et al. | 424/426 |
| 6,753,454 B1 | 6/2004 | Nelson et al. | 604/43 |
| 6,821,479 B1 | 11/2004 | Smith et al. | 422/21 |
| 7,765,647 B2 | 8/2010 | Smith et al. | 19/145 |
| 2002/0081732 A1* | 6/2002 | Bowlin et al. | 435/446 |
| 2005/0095695 A1* | 5/2005 | Shindler et al. | 435/285.1 |
| 2005/0208110 A1 | 9/2005 | Singh et al. | 424/443 |
| 2006/0153904 A1* | 7/2006 | Smith et al. | 424/448 |
| 2006/0204539 A1 | 9/2006 | Atala et al. | 424/423 |
| 2007/0207186 A1* | 9/2007 | Scanlon et al. | 424/424 |
| 2007/0213522 A1 | 9/2007 | Harris et al. | 536/56 |
| 2010/0018641 A1* | 1/2010 | Branham et al. | 156/244.17 |

FOREIGN PATENT DOCUMENTS

| | | | | |
|---|---|---|---|---|
| CA | 2575662 | | 2/2006 | ............. A45D 44/22 |
| CA | 2587029 | | 5/2006 | ............. A61K 33/34 |
| CA | 2599627 | | 9/2006 | ............. C11D 17/06 |
| EP | 1249232 | | 10/2002 | ............. A61K 9/51 |
| WO | WO 01/54667 | * | 8/2001 | ............. A61K 9/14 |
| WO | WO02/40242 | * | 5/2002 | ............. B29C 41/00 |
| WO | WO 03/011233 | | 2/2003 | ............. A61K 8/25 |
| WO | WO 2007/034736 | | 3/2007 | ............. A61K 9/70 |

OTHER PUBLICATIONS

Li et al., "Electrospinning of Nanofibers: Reinventing the whell?," *Advanced Materials* 16, 1151-1170 (2004).

* cited by examiner

*Primary Examiner* — Anna Falkowitz
(74) *Attorney, Agent, or Firm* — Medlen & Carroll, LLP

(57) ABSTRACT

The present invention relates to methods and compositions for the delivery of cosmetics and medicants. In some embodiments, the invention relates to compositions comprising both hydrophobic and hydrophilic polymers. In preferred embodiments, the invention relates to the delivery of peptides, small molecules and other bioactive compounds using the compositions and methods disclosed herein.

26 Claims, 5 Drawing Sheets

The integrated multi fiber matrix

COMPOSITIONS AND METHODS FOR THE DELIVERY OF AGENTS

FIELD OF THE INVENTION

The present invention relates to methods and compositions for the delivery of cosmetics and medicants. In some embodiments, the invention relates to compositions comprising hydrophilic polymers, as well as compositions comprising both hydrophobic and hydrophilic polymers. In preferred embodiments, the invention relates to the delivery of vitamins, peptides, small molecules, medicants and other bioactive compounds, whether alone, in mixtures, or encapsulated (e.g. encapsulated in microspheres or nanospheres) using the compositions and methods disclosed herein.

BACKGROUND OF THE INVENTION

Cosmetics and skin care compositions are among the world's most widely researched and commercialized commodities. The significant cost of many of these compositions necessitates that they be delivered to a subject in an effective manner. However, the physical and/or chemical limitations as well as the ease and safety of many traditional delivery systems obviates their use in the administration of many dermally applied entities, particularly in view of their rapid development and improvement as well as their ever-increasing demand worldwide. Thus, there is a need to identify compositions that effectively facilitate the delivery of cosmetics and skin care compositions.

SUMMARY OF THE INVENTION

The present invention relates to methods of making transdermal and topical delivery devices, as well as methods and compositions for the delivery of agents, including cosmetic agents (e.g. vitamins, dermal fillers, botox, etc.) and medicants. In some embodiments, the invention relates to compositions comprising hydrophilic polymers, as well as compositions comprising both hydrophobic and hydrophilic polymers. In preferred embodiments, the invention relates to the delivery of vitamins, peptides, small molecules and other bioactive compounds, whether alone, in mixtures, or encapsulated (e.g. encapsulated in microspheres or nanospheres), using the compositions and methods disclosed herein. In further embodiments, the invention relates to compositions comprising clay and comprising a bioactive agent for the treatment of skin diseases and disorders. Cosmetic treatment (e.g. reduce wrinkles) is also contemplated.

In one embodiment, the present invention contemplates a dissolving or "disappearing" (e.g. the outline of the material and the material itself becomes invisible as the material transforms from solid, or semi-solid, to liquid) film or patch for use on the skin to deliver compounds (e.g. vitamins, peptides, drugs, etc.). In one embodiment, the dissolving film or patch comprises hydrophilic polymer fibers, e.g. a polymer fiber matrix that is porous, but mechanically strong enough to apply to the skin without tearing. Structural materials for the patch are selected in order to achieve desired patch dissolution rate on the skin (e.g. less than 10 seconds, approximately 10 seconds, 10 minutes, 10 hours, 10 days). The more hydrophilic, the faster (e.g. 1-20 seconds) the dissolution; conversely, the more hydrophobic, the slower (minutes to hours to days) the dissolution. In one embodiment, a polymer (or mix of polymers) is employed in a structural portion of the patch, which dissolves on the skin at a pre-determined rate. In a preferred embodiment, the skin is pretreated to make it moist or wet (e.g. with a light spray or aerosol, comprising water and other optional ingredients). In one embodiment, one or more active ingredients are incorporated or trapped within the matrix. For example, the present invention contemplates embodiments wherein the active ingredients are a) incorporated into the structural backbone of the fibers (or simply absorbed on the fibers) and/or b) integrated into (or trapped within) the voids of the structure. The amount which goes into a) or b) can be controlled (e.g. depending on the nature of the fibers, the porosity of the matrix, the interaction of the fibers with the active ingredients, and the like). Where microspheres or nanospheres are employed, the amount which goes in may depend on how fast and thoroughly the spheres dissolve, as well as the content of the spheres. In this way, the present invention contemplates, in one embodiment, 1) burst release (of active ingredients) out of the voids followed by 2) slower release out of the fibers as they dissolve.

The present invention relates to a novel method of manufacturing a transdermal drug delivery matrix and alleviates many of the difficulties currently faced during the preparation of transdermal drug delivery matrices. In addition, the present method of manufacture yields uniform compositions of transdermal polymer mixtures containing an active agent, prepared without using large quantities of solvents, and without loss of the active agent due to exposure to temperature variations. Due to their extreme porosity the self-dissolving transdermal matrices prepared by these methods perform better in transdermal devices and show greater flux of active agent. 100% flux of the drug out of self-dissolving matrices prepared by the method of the present invention can be demonstrated. As a result of the improved performance, less active agent can be utilized during the manufacturing process.

Thus, in contrast to typical skin patches, where only a small amount (1-10%) of active ingredient is employed and only a portion (10-50%) is delivered, the present invention contemplates films or patches wherein the active ingredient is the major component of the patch composition (e.g. greater than 50%, more preferably at least 70%, still more preferably at least 80%, and most preferably between 80 and 95%) and the vast majority of the active ingredient (80-100%) is delivered into the skin. In one embodiment, the preferred film or patch should incorporate (or carry) the active ingredient(s) without involvement of softeners, plasticizers and preservatives.

In one embodiment, the present invention also contemplates a film or patch wherein only a portion dissolves or "disappears" quickly (seconds to minutes). For example, the dissolving portion is hydrophilic, whereas the stable portion (hours to days) is hydrophobic.

The films and patches of the present invention can be used alone or with other modes of delivery, including but not limited to microneedles, iontophoresis, electroporation, and the like. For example, in one embodiment, microneedles (discussed more below) are applied to the skin and the film or patch is placed on top of the microneedles (which may be pre-treated to facilitate the dissolution of the patch and release of active ingredients) so that compounds (including high molecular weight compounds) are delivered more readily (and more deeply) into the skin. In another embodiment, the film or patch is part of an iontophoresis patch (discussed more below).

The films and patches of the present invention can be used alone or with "activators." For example, in a preferred embodiment, the skin is pretreated to make it moist or wet (e.g. with a light spray or aerosol, comprising water and other optional ingredients). Such optional ingredients include, but are not limited to: NaPCA [available commercially as Twinlab NaPCA with the following ingredients: Purified water, NaPCA (the sodium salt of pyrrolidone carboxylic acid), eucalyptus, ethanol, monolaurin (the principal antimicrobial factor in mother's milk)]; isopropyl alcohol; Beta Glucan [which is available as Beta-glucan, with 1,3- and 1,6-glucose links, which can be isolated from a variety of fungi such as shiitake (*Lentinus edodes*) and maitake (*Grifola frondosa*) mushrooms, or from yeast cell walls including brewers' and bakers' yeasts (of the genus *Saccharomyces*), and from oat and barley bran]; Butylene glycol; hyluronic acid and the like (all of which can be combined together in various combinations).

In one embodiment, the present invention contemplates formulating films and patches (and similar media) using polymers that are capable of absorbing water (hydroscopic or hydrophilic) as well as capable of absorbing oil when diluted in a solvent. In one embodiment, the active ingredients) is mixed in or formulated with the matrix, and the active (whether based on water, oil or solids) is released and eluted/ delivered when the media is applied to humid (moist or wet) tissue.

In some embodiments, the invention relates to a composition (e.g. a skin care composition) comprising a first layer under a second layer, said first layer comprising a biomaterial (including but not limited to a material selected from the group consisting of collagen, cellulose and algenate, as well as nanospheres thereof), said second layer comprising polymeric fibers, said fibers selected from the group consisting of microfibers and nanofibers. In a preferred embodiment, said second layer comprises electrospun microfibers (or nanofibers) In further embodiments, said polymeric microfibers (or nanofibers) comprises a hydrophilic polymer. In still further embodiments, said polymeric microfibers (or nanofibers) comprises a hydrophobic polymer. In additional embodiments, said polymeric microfibers (or nanofibers) possess adhesive properties upon wetting. In additional embodiments, said polymeric microfibers (or nanofibers) can be impregnated with a solution of active ingredient(s) for controlled or sustained delivery of active ingredient(s). In some embodiments, said active ingredient(s) is stored dry (e.g. as a solid formulation) and is activated upon wetting of said polymeric microfibers (or nanofibers) so as to form a solution of the active ingredient(s) in the microfiber (or nanofiber) for controlled or sustained delivery of the active ingredient(s). In further embodiments, said polymeric microfibers (or nanofibers) form an invisible film upon wetting that further dissolves upon additional wetting. In still further embodiments, said polymeric microfibers (or nanofibers) containing active ingredient(s) are coated onto said first layer so as to form said second layer.

Today's available skincare plasters can have difficulty adhering to a sweating skin surface in connection with sports or burns. That is to say, they tend to slide away or off the skin, which limits the time for the active drug in the plaster to activate. By adding a first top layer of PVP fibers, in one embodiment, the sweat is absorbed and the active drug is accelerated.

It is not intended that the composition be limited by the nature of the polymer(s) used for the microfibers (or nanofibers). A variety of polymers can be used. Indeed, multiple (different) polymers can be used together or separately. In a preferred embodiment, the composition is made using both hydrophobic and hydrophilic polymers (see FIG. 1). When a variety of polymers are used together (e.g. multiple kinds of polymers in the second layer), this allows for "tagging" each fiber with different active ingredients, allowing for a significant scope of functionality.

Is not intended that the present invention be limited by the nature of the biomaterial. In a preferred embodiment, the biomaterial is absorbent, and even highly absorbent. In such an embodiment, the present invention contemplates combining highly absorbent "sponges" with solid microfiber (or nanofiber) platforms to obtain advantages over other delivery technologies.

It is also not intended that the present invention be limited by the number of layers. Single, double, triple layer (or more) delivery devices are contemplated. The present invention, in one embodiment, contemplates a method for fabricating a three layer matrix (FIG. 5C), wherein three layers are electrospun from three different solutions via three tips on to one and same collector. In one embodiment, the process begins by adding first layer to the collector, then continuing by adding the first combined with the second layer, and then gradually removing the first layer while continuing with a second layer alone, then continuing with a combined second and third layer, and then gradually removing the second layer and continuing with a third layer. In one embodiment, the present invention contemplates a three-layer matrix, said matrix comprising thrombin in one of the three layers.

It is not intended that the present invention be limited by the method by which active agent is added. In some embodiments, the active agent is added in dry form (this permits the use of agents which are not stable, or as stable, in solution). In some embodiments, the agent is added in solution and then allowed to dry. In some embodiments (FIG. 3), the polymeric fibers are treated with water prior to adding the active agent (s). In some embodiments, the active agent(s) is sprayed onto the skin (e.g. in a mist, spray or aerosol) and the film or patch is placed on top of the area that contains the agent, whereupon the film or patch dissolves and facilitates the delivery of the active agent (even though the active agent was not formulated into, onto, or within the film or patch).

In one embodiment, the skin patch comprising polymeric fibers (an one or more active ingredients) is applied to the skin without pre-wetting the skin. This embodiment allows for "on command" delivery. When delivery is desired, the patch (or portion thereof) is sprayed (or otherwise contacted) with water (or an aqueous solution containing such optional ingredients as described herein) in order to trigger dissolution and delivery (e.g. in a bolus) of the active ingredient(s). A variety of active ingredients can be delivered in this manner. Particularly preferred actives for this approach include agents that reduce pain, and agents (e.g. nicotine) that reduce the desire for addictive (e.g. smoking) behavior or compulsive behavior. In one embodiment, agents that combat depression are contemplated in this mode of delivery. In another embodiment, agents that combat fatigue (e.g. for large equipment operators, truck drivers, train engineers, etc.) are contemplated in this mode of delivery.

It is also not intended that the present invention be limited by the nature or number of the active agent(s). In one embodiment, the present invention contemplates co-formulation of incompatible drugs (e.g. drugs whose characteristics make it difficult to co-formulate in a solution) which is possible because of the fiber matrix. In one embodiment, combination of drugs and cosmetic active ingredients are used in the same patch; for example, if there is a drug that irritates the skin, the present invention contemplates in one embodiment co-formulating a soothing cosmetic ingredient that will repair and sooth the skin after drug is delivered. In one embodiment, the present invention contemplates agents that are currently injected into the skin (e.g. botox, which can be made recombinantly as described in U.S. Pat. No. 5,919,665, hereby incorporated by reference); by using the patch, such injections are not needed (i.e. botox can be delivered without injections). In one embodiment, the present invention contemplates utilizing the fiber matrix to stabilize volatile drugs. In one embodiment, vitamins are obtained as fluids, water or oil or as solid crystals. In another embodiment, peptides, whether ribosomal and non-ribosomal (e.g. glutathione), are obtained in water solutions or as solids, or powder. In another embodiment, antibacterial and/or anti-inflammatory formulations are employed. Any number of active agents that induce a desired local or systemic effect may be used in the drug delivery devices manufactured by the method of the present invention. In particular, any compound that is suitable for transdermal administration may be employed. Active agents include, but are not limited to, compounds that may be classified as medicines, organic and inorganic drugs, hormones, nutrients, vitamins, food supplements, herbal preparations, and other agents that might benefit a human or animal. In general, such classifications include, but are not limited to, ACE inhibitors, adrenergics and anti-adrenergics, alcohol deterrents (for example, disulfiram), anti-allergies, anti-anginals, anti-arthritics, anti-infectives (including but not limited to antibacterials, antibiotics, antifungals, antihelmintics, antimalarials and antiviral agents), analgesics and analgesic combinations, local and systemic anesthetics, appetite suppressants, antioxidants, anxiolytics, anorexics, antiarthritics, anti-asthmatic agents, anticoagulants, anticonvulsants, antidiabetic agents, antidiarrheals, anti-emetics, antiepileptics, antihistamines, anti-inflammatory agents, antihypertensives, antimigraines, antinauseants, antineoplastics, antioxidants, antiparkinsonism drugs, antipruritics, antipyretics, antirheumatics, antispasmodics, antitussives, adrenergic receptor agonists and antagonists, anorexics, appetite suppressants, breath freshening agents (including but not limited to peppermint oil, spearmint oil, wintergreen oil and menthol), cardiovascular preparations (including anti-arrhythmic agents, cardiotonics, cardiac depressants, calcium channel blockers and beta blockers), cholinergics and anticholinergics, contraceptives, cough and cold preparations, diuretics, decongestants, growth stimulants, herbal preparations, hormones including but not limited to androgens, estrogens and progestins, steroids and corticosteroids, hypnotics, immunizing agents, immunomodulators, immunosuppresives, muscle relaxants, neurologically-active agents including anti-anxiety preparations, antidepressants, antipsychotics, psychostimulants, sedatives and tranquilizers, sore throat medicaments, sympathomimetics, vaccines, vasodilators, vasoconstrictors, vitamins, xanthine derivatives and combinations thereof.

The amount of active agent incorporated will vary, depending on the active agent chosen, the potency of the compound, the intended dosage, the group of individuals undergoing treatment, the particular indication, and the like. Such amounts are easily determined by one of ordinary skill in the art (see, for example, Volume 18 of Drugs and the Pharmaceutical Sciences, entitled "Dermatological Formulations: Percutaneous Absorption" (1983) Marcel Dekker, Inc. and the Handbook of Pressure Sensitive Adhesive Technology, 2nd Edition (1989) Van Nostrand, Reinhold).

Additional representative active agents include, by way of example and not for purposes of limitation, bepridil, diltiazen, felodipine, isradipine, nicardipine, nifedipine, nimodipine, nitredipine, verapamil, dobutamine, isoproterenol, carterolol, labetalol, levobunolol nadolol, penbutolol, pindolol, propranolol, solatol, timolol, acebutolol, atenolol, betaxolol, esmolol, metoprolol, albuterol, bitolterol, isoetharine, metaproterenol, pirbuterol, ritodrine, terbutaline, alclometasone, aldosterone, amcinonide, beclomethasone dipropionate, betamethasone, clobetasol, clocortolone, cortisol, cortisone, corticosterone, desonide, desoximetasone, 11-desoxycorticosterone, 11-desoxycortisol, dexamethasone, diflorasone, fludrocortisone, flunisolide, fluocinolone, fluocinonide, fluorometholone, flurandrenolide, halcinonide, hydrocortisone, medrysone, 6a-methylprednisolone, mometasone, paramethasone, prednisolone, prednisone, tetrahydrocortisol, triamcinolone, benoxinate, benzocaine, bupivacaine, chloroprocaine, cocaine, dibucaine, dyclonine, etidocaine, isobutamben, lidocaine, mepivacaine, pramoxine, prilocalne, procaine, proparacaine, tetracaine, zolamine hydrochloride, alfentanil, chloroform, clonidine, cyclopropane, desflurane, diethyl ether, droperidol, enflurane, etomidate, fentanyl, halothane, isoflurane, ketamine hydrochloride, mepridine, methohexital, methoxyflurane, morphine, propofol, sevoflurane, sufentanil, thiamylal, thiopental, acetominophen, allopurinol, apazone, aspirin, auranofin, aurothioglucose, colchicine, diclofenac, diflunisal, etodolac, fenoprofen, flurbiprofen, gold sodium thiomalate, ibuprofen, indomethacin, ketoprofen, meclofenamate, mefenamic acid, mesalamine, methyl salicylate, nabumetone, naproxen, oxyphenbutazone, phenacetin, phenylbutazone, piroxican, salicylamide, salicylate, salicylic acid, salsalate, sulfasalazine, sulindac, tolmetin, acetophenazine, chlorpromazine, fluphenazine, mesoridazine, perphenazine, thioridazine, trifluorperazine, triflupromazine, diisopyramide, encainide, flecainide, indecanide, mexiletine, moricizine, phenytoin, procainamide, propafenone, quinidine, tocainide, cisapride, domperidone, dronabinol, haloperidol, metoclopramide, nabilone, prochlorperazine, promethazine, thiethylperazine, trimethobenzamide, buprenorphine, butorphanol, codeine, dezocine, diphenoxylate, drocode, hydrocodone, hydromorphone, levallorphan, levorphanol, loperamide, meptazinol, methadone, nalbuphine, nalmefene, nalorphine, naloxone, naltrexone, oxybutynin, oxycodone, oxymorphone, pentazocine, propoxyphene, isosorbide dinditrate, nitroglycerin, theophylline, phenylephrine, ephidrine, pilocarpine, furosemide, tetracycline, chlorpheniramine, ketorolac, ketorolac tromethamine, bromocriptine, guanabenz, prazosin, doxazosin, flufenamic acid, benzonatate, dextromethorphan hydrobromide, noscapine, codeine phosphate, scopolamine, minoxidil, combinations of the above-identified active agents, and pharmaceutically acceptable salts thereof.

Other representative agents include, but are not limited to, benzodiazepines, such as alprazolan, brotizolam, chlordiazepoxide, clobazam, clonazepam, clorazepate, demoxepam, diazepam, flumazenil, flurazepan, halazepan, lorazepan, midazolam, nitrazepan, nordazepan, oxazepan, prazepam, quazepan, temazepan, triazolan, pharmaceutically acceptable salts thereof, and combinations thereof; anticholinergic agents such as anisotropine, atropine, belladonna, clidinium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, telezepine, tridihexethyl, tropicamide, combinations thereof, and pharmaceutically acceptable salts thereof; estrogens, including but not limited to, 17p-estradiol (or estradiol), 17a-estradiol, chlorotrianisene, methyl estradiol, estriol, equilin, estrone, estropipate, fenestrel, mestranol, quinestrol, estrogen esters (including but not limited to estradiol cypionate, estradiol enanthate, estradiol valerate, estradiol-3-benzoate, estradiol undecylate, and estradiol 16,17-hemisuccinate), ethinyl estradiol, ethinyl estradiol-3-isopropylsulphonate, pharmaceutically acceptable salts thereof, and combinations thereof; androgens such as danazol, fluoxymesterone, methandrostenolone, methyltestosterone, nandrolone, nandrolone decanoate, nandrolone phenproprionate, oxandrolone, oxymetholone, stanozolol, testolactone, testosterone, testosterone cypionate, testosterone enanthate, testosterone propionate, 19-nortestosterone, pharmaceutically acceptable salts thereof, and combinations thereof; and progestins such as cingestol, ethynodiol diacetate, gestaclone, gestodene, bydroxyprogesterone caproate, levonorgestrel, medroxyprogesterone acetate, megestrol acetate, norgestimate, 17-deacetyl norgestimate, norethindrone, norethindrone acetate, norethynodrel, norgestrel, desogestrel, progesterone, quingestrone, tigestol, pharmaceutically acceptable salts thereof, and combinations thereof.

In another embodiment, nicotine is added into the hydrophilic fibers as to instantly release as a bolus to meet the nicotine demands of a smoker. In a yet another embodiment, antibacterial, antibiotic, pain control, scar-reduction formulations are employed. In still another embodiment, a multi layer matrix releases thrombin, such as RECOTHROM™ manufactured by Zymogenetic Inc, or Tisseel (a two component fibrin biomatrix manufactured by Baxter Inc.) so as to stop diffused bleeding. In this latter embodiment, it is preferred that thrombin is on one surface, while a high molecular weight Hyaluronic Acid (e.g. manufactured by NovoZymes) is used on the upperside surface hindering friction and tissue adherence.

In some embodiments, the invention relates to a method for administering a compound, comprising: a) providing i) a subject, and ii) a skin care composition according to the above (e.g. polymeric microfibers or nanofibers over a biomaterial, with one or more active agents) and b) administering said skin care composition to said subject (e.g. by bringing said first layer or second layer in contact with said subject). In further embodiments said composition is administered topically. In some embodiments, said composition is administered transdermally. In further embodiments, said compound or agent is a peptide, vitamin, organic acid, oil or medicant. In additional embodiments, said subject exhibits symptoms associated with or is suspected of having a skin disorder (or is at risk for such a disorder). In some embodiments, said skin disorder is selected from the group consisting of acne, bed sores, rash, dry skin, dermal abrasions, dermatitis, sunburn, scars, hyperkeratosis, granuloma and skin ulceration. In one embodiment, protectants are administered via the patch to protect from sunburn (e.g. block UV). In further embodiments, said vitamin is selected from the group consisting of vitamin C, vitamin A, vitamin E, vitamin K and vitamin B complex. In still further embodiments, said organic acid is hyaluronic acid, and preferably low molecular weight (e.g. 50 kD) hyaluronic acid (which can be obtained from a variety of sources, including Degussa in Germany). In one embodiment, the present invention contemplates utilizing methods and compositions to stabilize vitamins and/or improve delivery through the skin. Methods and compositions for stabilizing vitamins are described in WO/2003/011233 (and in patents cited within this PCT application), all of which are hereby incorporated by reference. In one embodiment, vitamin derivatives are employed (e.g. retinoic ester is a derivative of vitamin A). In one embodiment, encapsulated vitamins are employed, including but not limited to encapsulated vitamin C available from Nanohybrid Co. (Seoul, Korea). In another embodiment, agents are encapsulated using the methodology of Sol-Gel Technologies Ltd.

In some embodiments, the invention relates to a composition (e.g. a skin care composition) comprising a first layer under a second layer (FIG. 5B), said first layer comprising a first polymer (including but not limited to hydrophilic synthetic polymers such as PVP, or other "skin friendly" polymers), said second layer comprising a second polymer. In a preferred embodiment, said second polymer comprises electrospun polymeric microfibers (or nanofibers). In some embodiments, said second layer further comprises one or more active ingredients. In some embodiments, said first layer comprises one or more active ingredients (and the second layer lacks active agents, maintains its structural integrity, and serves simply as an occlusive layer). In yet other embodiments, both said first and second layer comprise one or more active ingredients (e.g. both contain the same active agents, or each contain different active agents). In one preferred embodiment, both layers contain the same active agent, wherein the release kinetics are different (for example, where the first layer is PVP, contact with the skin typically causes the PVP to dissolve, or partially dissolve, thereby releasing active agent in a "burst"—while the second layer is more stable and provides for sustained release, and longer term release if encapsulated in nanospheres). In preferred embodiments, both the first and second layers comprise electrospun polymers, such that said polymers are microfibers (or nanofibers). In some embodiments, said active ingredient(s) is stored dry (e.g. as a solid formulation) in the second layer and is activated upon wetting of said polymeric microfibers (or nanofibers) so as to form a solution of the active ingredient(s) in the microfiber (or nanofiber) for controlled or sustained delivery of the active ingredient(s). In further embodiments, said polymeric microfibers (or nanofibers) of said first layer form an invisible film upon wetting that further dissolves upon additional wetting.

While electrospun matrices are preferred, some active agents (e.g. medication cocktails) cannot tolerate the electrical field used in electrospinning. Therefore, in one embodiment, the present invention contemplates utilizing ultrasonic coating. In one embodiment, both techniques are employed, i.e. at least one nano electro spinning tip together with at least one ultra-sonic nozzle (e.g. from SONO-TEK Corporation) which let the spheres fall on to the drum, the collector.

In some embodiments, the invention relates to a method for administering a compound, comprising: a) providing i) a subject, and ii) a skin care composition according to the above (e.g. first and second layers, each comprising polymeric microfibers or nanofibers, with one or more active agents in one or both layers) and b) administering said skin care composition to said subject (e.g. by bringing said first layer or second layer in contact with said subject). In further embodiments said composition is administered topically. In some embodiments, said composition is administered transdermally, or subcutaneously between tissues (e.g. by surgical intervention).

Again, it is not intended that the present invention be limited by the particular polymer used. Table 1 provides (non-limiting) examples of useful polymers for various embodiments of the present invention. In one embodiment, the film or patch can be completely made out of ingredients that are recognized as cosmetically active or at least very skin friendly (e.g. a structural portion of the patch can be made out of hyaluronic acid polymer, or aloe vera polymer or any other natural polymer).

In one embodiment, the present invention contemplates using aliphatic polyether polyurethane as a polymer to make the fiber matrices for a film or patch to deliver active ingredient(s). TECOGEL® 200 is a commercially available (manufactured by Thermedics Polymer Products, Wilmington, Mass.) form of aliphatic polyether polyurethane that is capable of absorbing 200% of its weight in water. Similarly available are TECOGEL® 500, which is capable of absorbing 500% of its weight in water, and TECOGEL® 2000, which is capable of absorbing 2000% of its weight in water. Other TECOGEL® polymers can be engineered with water absorption less than 200% and more than 2000% and could be utilized with the present invention for specific applications. Medical grade aliphatic polyether based hydrogel TPUs are available from Lubrizol under the name Tecophilic® TG-500 or TG-2000, which can absorb water up to 900% of the weight of the dry resin.

In one embodiment, the present invention contemplates a skin patch comprising a matrix of fibers and one or more active ingredients, wherein said fibers are hydrophilic fibers capable of becoming an invisible film upon wetting that further dissolves completely (i.e. no solid structural portion is visible to the eye) in less than one minute (e.g. less than 30 seconds, or more preferably between 1 and 20 seconds). In a preferred embodiment, said matrix lacks hydrophobic fibers. In a particularly preferred embodiment, said matrix is made (e.g. exclusively) of electrospun PVP fibers. Again, it is not intended that the present invention be limited by the nature or number of active ingredients (e.g. said active ingredient is a cosmetic, peptide, vitamin, organic acid, oil or medicant). The present invention contemplates using such a patch or film to deliver actives into the skin. Thus, in one embodiment, the present invention contemplates a method for delivering an active ingredient into the skin: a) providing i) a subject (who may healthy or may have a disorder), and ii) the skin patch described above; and b) administering said skin patch to said subject under conditions such that said active ingredient is delivered into the skin. In one embodiment, said conditions of step b) comprise pre-wetting skin of said subject prior to applying said skin patch. In one embodiment, said pre-wetting comprises spraying an aqueous solution onto said skin (e.g. wherein said spraying results in a mist or aerosol).

As noted above, the active ingredients need not be included in the patch (or at least some actives can be outside the patch, whether the patch has additional actives or not). Thus, in one embodiment, the present invention contemplates a method for delivering an active ingredient into the skin: a) providing a subject (who may be healthy or who may have a disorder), a solution comprising an active ingredient; and a skin patch comprising electrospun hydrophilic fibers; b) pre-wetting skin of said subject with said solution; and c) administering said skin patch to said subject under conditions such that said active ingredient is delivered into the skin. Again, said pre-wetting comprises spraying said solution onto said skin (e.g. wherein said spraying results in a mist or aerosol).

The present invention also contemplates kits comprising the various films or patches described herein. Thus, in one embodiment, the present invention contemplates a kit, comprising a pre-wetting solution, and a skin patch, said skin patch comprising electrospun hydrophilic fibers. In one embodiment, said pre-wetting solution comprises an active ingredient. In one embodiment, said patch comprises an active ingredient. In one embodiment, the kit further comprises instructions for pre-wetting skin and applying said patch under conditions to form an invisible film that dissolves completely in less than one minute (e.g. less than 30 seconds, or more preferably between 1 and 20 seconds).

BRIEF DESCRIPTION OF THE DRAWINGS

For a more complete understanding of the features and advantages of the present invention, reference is now made to the detailed description of the invention along with the accompanying figures.

DEFINITIONS

Figure 1:
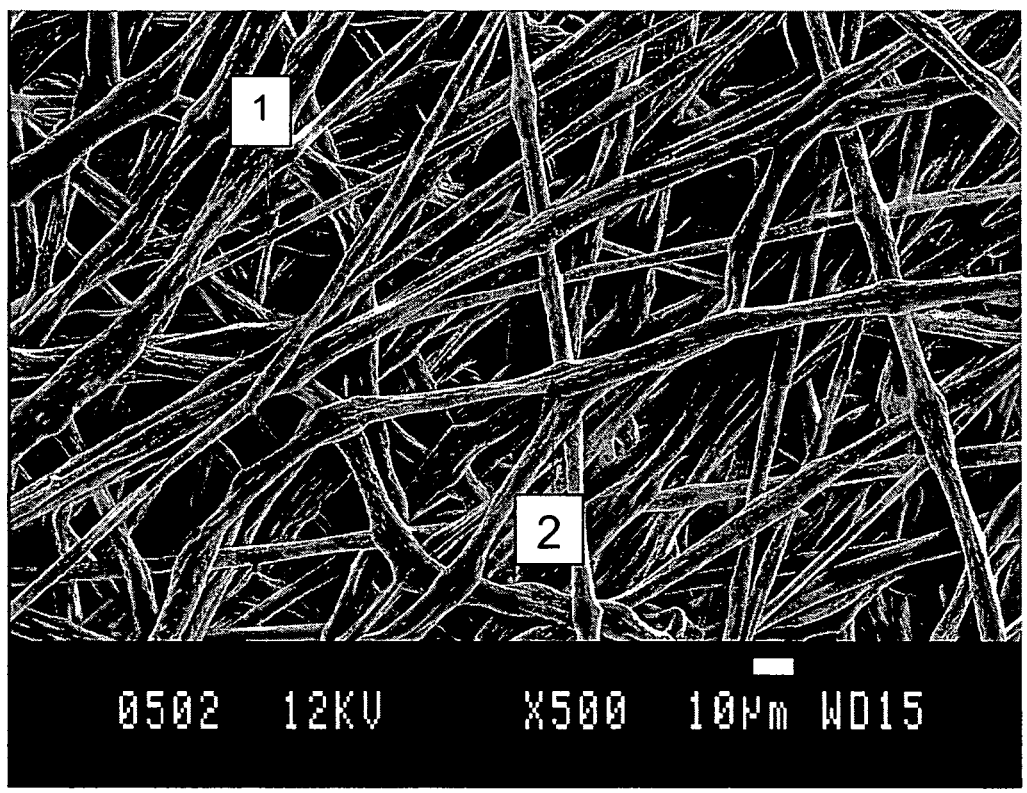
FIG. 1 shows a micrograph of one embodiment of the present invention, in which a composition comprised of a hydrophobic fiber (1) and a hydrophilic fiber that has been impregnated with a bioactive ingredient (2).
Figure 2:
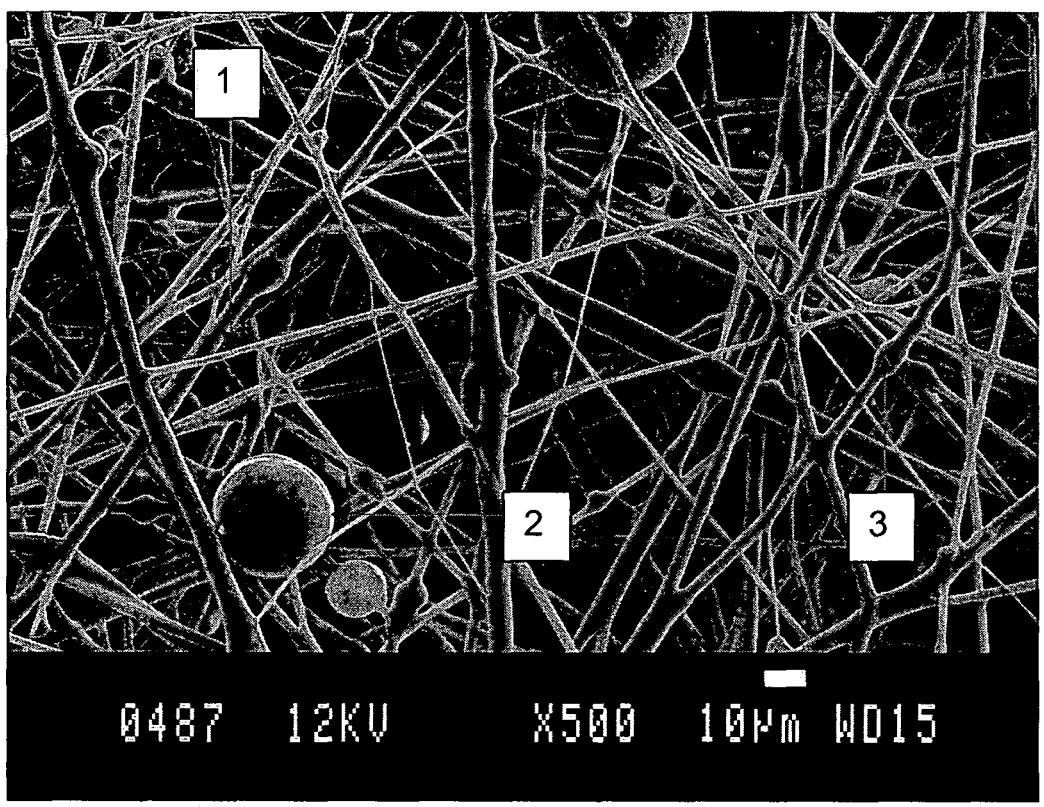
FIG. 2 shows a micrograph of one embodiment of the present invention, in which a composition comprised of a hydrophobic fiber (1), an adhering molecule nanosphere (2) and a hydrophilic fiber that has been impregnated with a bioactive ingredient (3).
Figure 3:
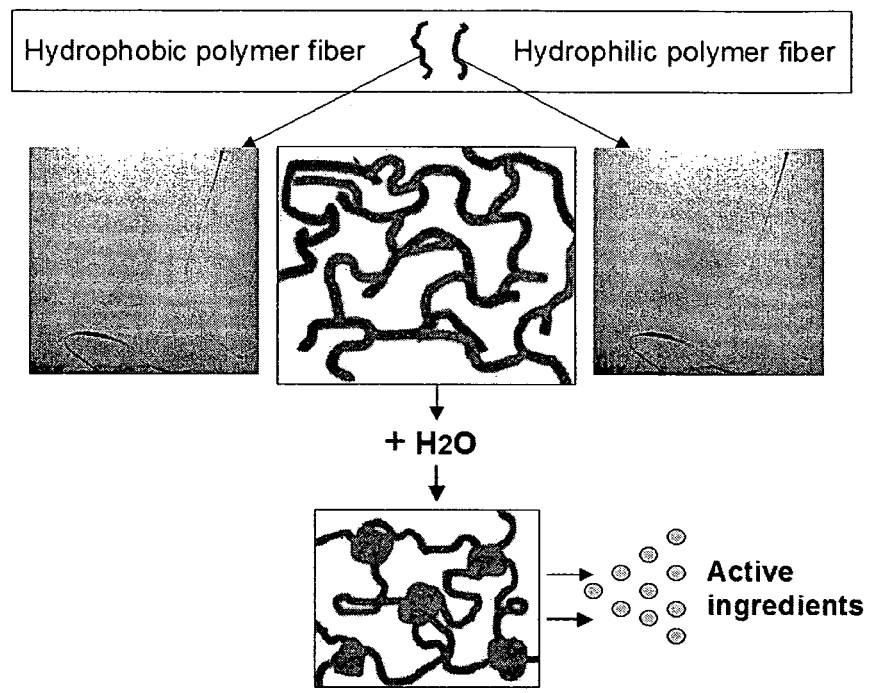
FIG. 3 shows a schematic depicting the compilation of the present invention, in which both a hydrophobic and a hydrophilic polymer are integrated. The resulting composition is ordered under aqueous conditions followed by incorporation of the bioactive ingredient(s).
Figure 4:
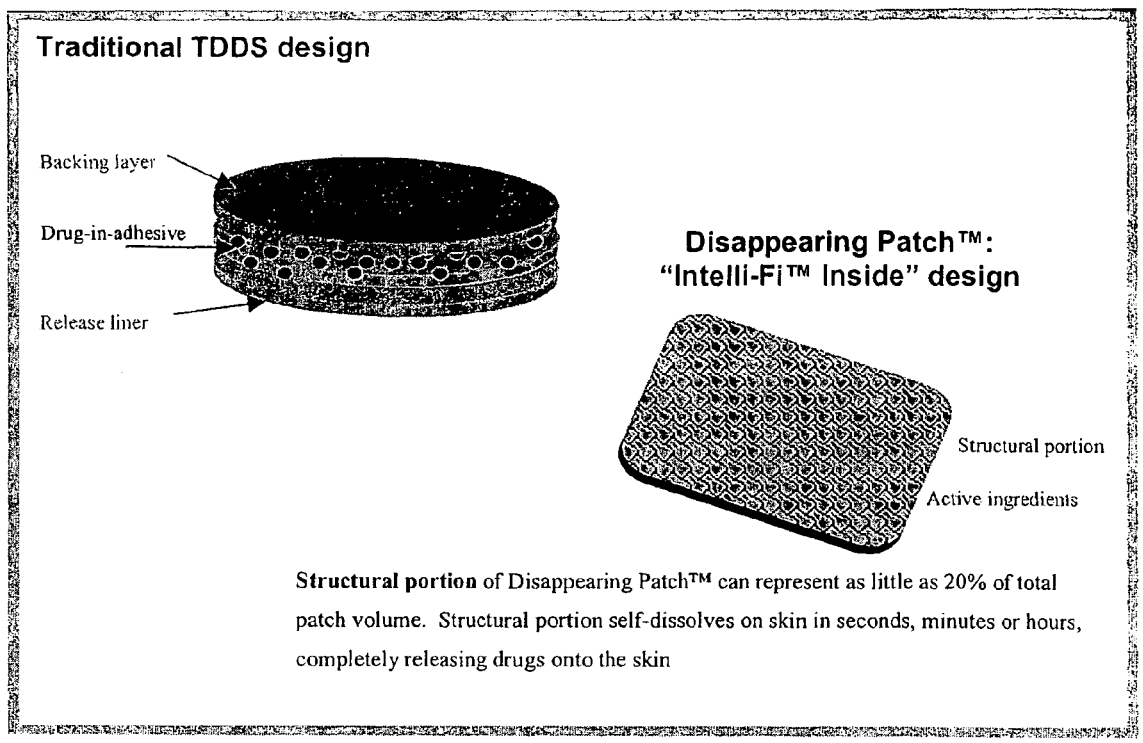
FIG. 4 shows a schematic comparing traditional transdermal devices (which has a great deal of structure compared to active ingredients) with one embodiment of the patch according to the present invention (wherein the structural portion can represent as less than 50%, more preferably less than 30%, and as little as approximately 20%, of total patch volume) which illustrates a 3-dimensional, single layer matrix, into which multiple functions are integrated by modulating formulations and processing conditions during the patch manufacturing. For instance the uppermost section of the patch (the equivalent of backing layer in traditional devices) features properties that enable desired level of patch occlusiveness, or no occlusive properties at all. Adhesive properties of the lower patch section that contacts skin are controlled in a similar fashion.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, a "cosmetic" refers to a substance that aids in the enhancement or protection of the appearance (e.g. color, texture, look, feel, etc.) or odor of a subject's skin. A cosmetic may change the underlying structure of the skin.

A "skin disorder" refers to a disease or condition that affects the health of a subject's skin. In a preferred embodiment, the present invention comprises methods and compositions for the treatment of conditions that affect skin care, which include but are in no way limited to acne, bed sores, rash, dry skin, dermal abrasions, dermatitis, sunburn, scars, hyperkeratosis, granuloma and skin ulceration.

Nanospun fiber diameters can range from 5 to 1000 nm; thereby adding an extremely high surface area to a polymeric surface but more importantly giving the opportunity to combine unmixable polymers and drug cocktails into "semi-homogeneous" matrices with extreme volume containments. Nano spinning combines the process of using a high electric force generated between capillary tips dispensing a polar polymer solution drawn towards the other pole, the receiver. The fiber diameter and the spun matrix porosity can be controlled by regulating the voltage, solution and solvent composition together with humidity, temperature and pressure in the environment of the process.

As used herein, the term "microfibers" refers to a fiber with a diameter in microns (e.g. 1 to 20 microns, but more typically between approximately 5 and 10 microns). The term "nanofiber" refers to a fiber with a diameter of less than 100 nanometers. In a preferred embodiment, said microfibers or nanofibers are produced via electrospinning, a process in which an electrical charge is used to generate a mat of said fibers as described in Li et al. *Advanced Materials* 16, 1151-1170 (2004), and by Smith in U.S. Pat. No. 6,753,454, hereby incorporated by reference. Electrospinning generally involves the introduction of a polymer or other fiber-forming liquid into an electric field, so that the liquid is caused to produce fibers. These fibers are drawn to an electrode at a lower electrical potential for collection. During the drawing of the liquid, the fibers rapidly harden and/or dry. The hardening/drying of the fibers may be caused by cooling of the liquid, i.e., where the liquid is normally a solid at room temperature; by evaporation of a solvent, e.g., by dehydration (physically induced hardening); by a curing mechanism (chemically induced hardening); or by a combination of these methods. Electrostatically spun fibers can be produced having very thin diameters.

As can be understood the nano spinning process makes it possible to create a matrix with a variety of ingredients that are either a) contained into a matrix of fibers either as suspended particles, spheres, or free fluid between the fibers, b) particles, spheres or free fluid incorporated or coated into the bulk of the fiber from a mixed solution, or c) allowed to fill hollow fibers made by concentric capillary dispenser tips. The process runs at room temperature with no risk for harming the chemistry by heat. The solvents are selected with the view on whether to dilute oil or water into the spinning solution which also can draw fibers at a voltage lower than 1 KV/cm between the dispenser tip to the receiver. The charge will not harm to the chemistry.

The term "hydrophobic" refers to the physical property of a molecule that is repelled from a mass of water. In a preferred embodiment, hydrophobic polymers are incorporated into the compositions of the present invention. While not limited to any particular polymer, examples of hydrophobic polymers include PolyCarbothane (aliphatic, polycarbonate-based TPU), Shore A 75 through Shore D 72 (manufactured by Thermedics Polymer Products, Wilmington, Mass.), Poly (Vinyl Acetate), PolySulfone (manufactured by Solvay Advanced Polymers Gmbh Düsseldorf Germany), Poly(Vinyl Chloride) and biodegradable Polylactide (PLA) manufactured by Boehringer Ingelheim GmbH, Ingelheim Germany).

"Hydrophilic" refers to the physical property of a molecule that is able to transiently associate with water (e.g. bond with water via hydrogen bonding). In a preferred embodiment, hydrophilic polymers are incorporated into the compositions of the present invention. While not limited to any particular polymer, examples of hydrophilic polymers include Poly (Ethylene Glycol), Poly(Propylene Glycol), Poly(Vinyl Alcohol), Polypyrrolidone or Polyvinylpyrrolidone (PVP), and the biodegradable PolyActive (a soft poly ethylene glycol-terephalate block copolymer with a hard poly buthylene-terephthalate) manufactured by OctoPlus Zernikedreef Holland. In a preferred embodiment, PVP is of sufficient molecular weight for electrospinning [Sigma #81440 K 90, mol wt ~360,000 (Fluka)].

A "solvent" is a liquid that dissolves a solid, liquid or gaseous solute, generating a solution. Solvents may include but are in no way limited to water and organic solvents including but not limited to chloroform (CHF), isopropanol (IPA), methanol (MEA), acetone and tetrahydrofuran (THF).

As used herein, the terms "prevent" and "preventing" include the prevention of the recurrence, spread or onset of a disease or disorder. It is not intended that the present invention be limited to complete prevention. In some embodiments, the onset is delayed, or the severity of the disease or disorder is reduced.

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

"Subject" refers to any mammal, preferably a human (whether healthy or not, whether a patient or not), livestock, or domestic pet.

As used herein, the term "topical" refers to administration of an agent or agents (e.g. cosmetic, medication, vitamin, etc.) on the skin. "Transdermal" refers to the delivery of an agent (e.g. cosmetic, medication, vitamin, etc.) through the skin (e.g. so that at least some portion of the population of molecules reaches underlying layers of the skin). It is not intended that the medication be limited to medicants that are delivered solely to the bloodstream, the medicant may be targeted, for example, to the skin or a subcutaneous area of a subject's skin. "Between tissues" refer to surgical interventions where an agent in a biodegradable dressing (e.g. medication) is applied to stop bleeding, leakage, unwanted adhesion between organs or cell disorders in connection anastomotic vascular bypass, implanted prostheses, or organs and cancer. In preferred embodiments, a specific dosage is delivered to and/or through the skin, or subcutaneously by surgical intervention. In one embodiment, the present invention contemplates self-dissolving patches/sheets to be placed onto organs in open surgeries for faster healing and delivery of drugs (during surgery or post-closure). This can be extended onto ophthalmic drug delivery where there is a need for an adhesiveness onto the wet surface of mucosa; the polymer formulations described herein can provide adhesion to such surfaces.

A "biomaterial" refers to a material that is produced by a living organism. It is not intended that the present invention be limited to materials that are produced by an organism per se, i.e. the present invention may comprise synthetic polymers that are inspired or were originally identified in organisms or biological settings. Examples of biomaterials include but are in no way limited to starches, collagen, cellulose, algenates, sugars, proteins, peptides and nucleic acids. Preferably, the biomaterial is used in dry form (e.g. free-dried collagen) during the manufacturing process for the composition. In one embodiment, the present invention contemplates utilizing compounds and compositions that stimulate collagen formation in the skin, including tretinoin (all-trans retinoic acid) and peptides such as hexapeptide 14 and the like. In one embodiment, Granactive Powder 168 (available from Grant Industries, Inc., New Jersey, USA), a powdered anti-aging complex that combines the matrix-fibroblast stimulation and collagen growth of palmitoyl hexapeptide-14 with plant derived fulvic acid (peat extract), is employed in the fiber matrices described herein to maximize the restorative powers of the skin's extra-cellular matrix (it also includes 24 carat colloidal gold to facilitate the electrolytic transfer between trace minerals and the skin's natural metallic-based electrolytes).

In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. In addition, auxiliary, stabilizing, thickening and coloring agents can be used. The present compositions, if desired, can also contain minor amounts of pH buffering agents.

"Impregnated" means filled or added to, but need not be limited to saturated conditions. Furthermore, it is not intended that the term be limited to encapsulation, although encapsulation is contemplated. In one embodiment, the polymeric microfiber or nanofiber web is impregnated by intercalation of the active ingredient or ingredients into the void spaces of said microfiber or nanofiber matrix (and/or into the fibers themselves).

DETAILED DESCRIPTION OF THE INVENTION

The present invention relates to methods and compositions for the delivery of agents, e.g. cosmetics and medicants. In some embodiments, the invention relates to compositions comprising both hydrophobic and hydrophilic polymers. In preferred embodiments, the invention relates to the delivery of peptides, small molecules and other bioactive compounds using the compositions and methods disclosed herein. In further embodiments, the invention relates to compositions comprising clay and further comprising a bioactive agent for the treatment of skin diseases and disorders.

In some embodiments, the invention relates to compositions that are impregnated with one or more active agents in dry form, or with a solution of one or more active ingredients for the controlled or sustained delivery of said active ingredients. Bioresorbable materials designed for the delivery of medicants and active agent delivery has previously been described as provided for in US Patent Application Number 2007/0213522 to Harris et al., incorporated herein by reference.

In some embodiments, the invention relates to the topical or transdermal delivery of a medicant for the purpose of treating a disease. The use of controlled-release skin patch delivery platforms have been previously described in U.S. Pat. No. 6,352,715 to Hwang et al., incorporated herein by reference.

In a preferred embodiment, the invention comprises a hydrophilic polymer. The polymer is selected such that it may dissolve in preparatory solvents, which include but are in no way limited to ethanol, isopropanol (IPA), methanol (MEA), acetone and tetrahydrofuran (THF). The solvent or solvents may further be used to dissolve active ingredients, providing a heterogeneous mixture of the polymer and the active ingredient. In a preferred embodiment, said active ingredients are oil based. The resulting polymeric fibers may be segmented into compositions comprising said active ingredients and said hydrophilic polymers and dried such that a microfiber or nanofiber is obtained. The polymer has the further ability to coat and encapsulate the (hydrophilic) dried particles.

In a preferred embodiment, the invention comprises a hydrophobic polymer. The polymer is selected for its tensile strength and stiffness such that it will keep the matrix in a stable form even when the hydrophilic polymer absorbs moisture, expands and applies stress to the integrated microfiber or nanofiber matrix. The stiffness and volume of the hydrophobic fiber further imparts flexibility and handling strength to the invention.

In a preferred embodiment, the present invention contemplates a microfiber or nanofiber web with two components: hydrophobic polymer is used as "structural", backbone, while a hydrophilic component is used to "encapsulate" the active ingredients. While not intended to limit the present invention to any particular mechanism, it is believed that, as the water enters the microfiber or nanofiber web, the hydrophobic structure remains intact. At the same time water "attacks" the hydrophilic branches and replaces the active ingredients—providing a release mechanism for the active agent. In one embodiment, the present invention contemplates a method of manufacture, wherein said two components are electrospun so as to create the polymeric microfibers or nanofibers.

Figure 5:
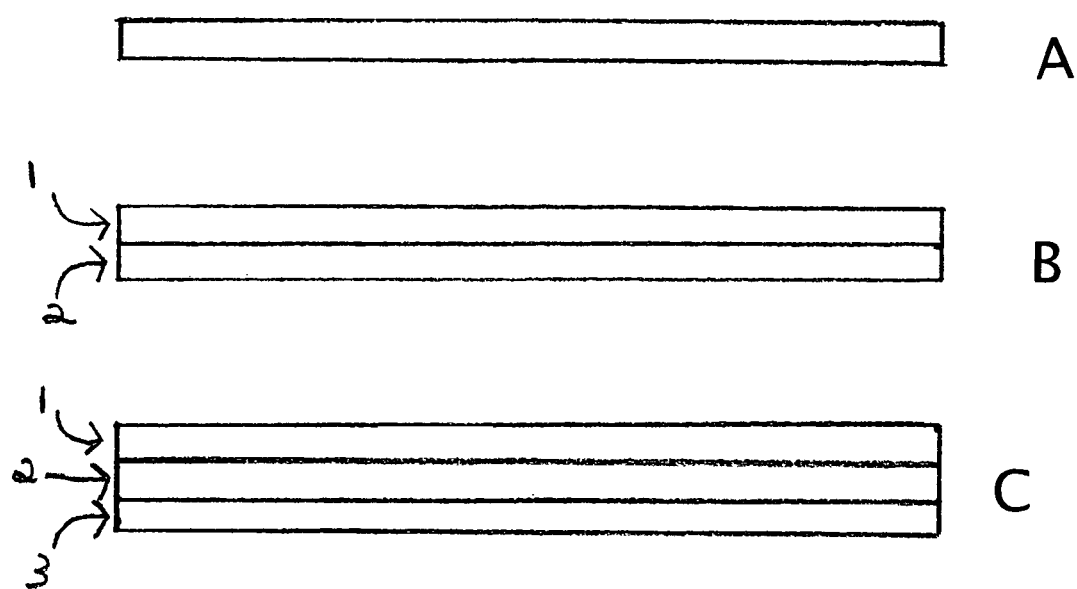
FIG. 5 shows a schematic depicting single layer (A), two layer (B), and three layer (C) devices according to the teachings herein.

In one embodiment, the present invention contemplates self-dissolving (i.e. upon application to the skin, and in particular, moist skin, it dissolves without the need for further manipulations, solvents or other chemicals) transdermal device comprises a homogeneous polymeric matrix or a heterogeneous polymeric matrix, all of which or sections of which are optimized to carry specific functions for the final product (patch or plaster). In one embodiment, the uppermost section of the patch features chemical properties to enable occlusive or non-occlusive environment under the patch. In one embodiment, intermediate patch layers (see FIG. 5) contain active agents that are incorporated into the structural backbone of the polymer or into the voids of the structure, which allows for control over release rate of active agents out of the matrix. In one embodiment, the bottom section of the patch secures the device to a surface (skin) provided by adhesive properties of the polymer used in segments of the bottom section of the device.

Enhancing Delivery

As noted above, the films and patches of the present invention can be used alone or with other modes of delivery, including but not limited to delivery enhancing compounds, microneedles, iontophoresis, electroporation, and the like. In another embodiment, the film or patch is part of an iontophoresis patch. Each of these approaches is discussed more below.

A. Delivery Enhancing Compounds

An optional enhancer may be combined with the films and patches described herein (or may be optionally applied to the skin prior to the application of the film or patch). It may be added to the polymer mixture during the optional blending step, or more preferably during or prior to the electrospinning step. The choice of enhancer to be optionally incorporated in the transdermal drug delivery matrix will depend upon the polymer and active agent to be administered. Suitable enhancers for use in this invention include, but are not limited to, dimethylsulfoxide (DMSO), dimethylformamide (DMF), N,N-dimethylacetamide (DMA), decylmethylsulfoxide (CloMSO), polyethylene glycol monolaurate (PEGML), propylene glycol (PG), propylene glycol monolaurate (PGML), methyl laurate, lauryl alcohol, glycerol monolaurate, linoleic acid, oleic acid, oleic acid dimers, oleyl alcohol, glycerol mono-oleate, glycerol dioleate, glycerol trioleate, lauryl lactate, myristyl latate, sorbitan monolaurate, sorbitan mono-oleate, lauramide diethanolamide, lecithin, the 1-substituted azacycloheptan-2-ones (preferably 1-n-dodecylcyclazacycloheptan-2-one, available under the trademark Azone (from Whitby Research Inc., Richmond, Va.), alcohols, lactate esters of C12 to C18 aliphatic alcohols, and the like. The permeation enhancer may also be a vegetable oil, as described in U.S. Pat. No. 5,229,130 to Sharma et al. Such oils include, by way of example and not for purposes of limitation, safflower oil, cotton seed oil and corn oil. In addition, combinations of enhancers as enumerated above, or as described in U.S. Pat. No. 5,053,227 to Chiang et al. and U.S. Pat. No. 5,693,335 to Xia et al., both of which are hereby incorporated by reference, may be used in the present invention.

The amount of enhancer present in the composition will depend on a number of factors, e.g. the strength of the particular enhancer, the desired increase in skin permeability, the rate of administration, and the type and amount of active agent to be delivered. The enhanced permeation effected through the use of such enhancers can be observed by measuring the rate of diffusion of active agent through animal or human skin using a Franz diffusion cell apparatus as described in U.S. Pat. No. 5,807,570 to Chen et al., hereby incorporated by reference. Such determinations are easily made by one of ordinary skill in the art (see, for example, Volume 62 of Drugs and the Pharmaceutical Sciences, entitled "Drug Permeation Enhancement: Theory and Applications" (1994) Marcel Dekker, Inc.).

B. Microneedles

In one embodiment, microneedles (discussed more below) are applied to the skin in the way that the film or patch is placed on top of the microneedles (which may be pre-treated to facilitate the dissolution of the patch and release of active ingredients) so that compounds (including high molecular weight compounds) are delivered more readily (and more deeply) into the skin. It is not intended that the present invention be limited to a particular microneedle design or product. An example is disclosed in U.S. Pat. No. 3,964,482 (by Gerstel), in which an array of either solid or hollow microneedles is used to penetrate through the stratum corneum, into the epidermal layer.

C. Iontophoresis

Iontophoresis is a non-invasive method of propelling high concentrations of a charged substance, normally medication or bioactive agents, transdermally by repulsive electromotive force using a small electrical charge applied to an iontophoretic chamber containing a similarly charged active agent and its vehicle. Iontophoresis performs desired medical treatment by driving (carrying) an ionizable or ionic drug, which has been applied on the skin, under predetermined electromotive force to deliver the same into the skin. For example, positively charged ions are driven (carried) into the skin on the side of an anode in an electric system of an iontophoresis device. Negatively charged ions, on the other hand, are driven (carried) into the skin on the side of a cathode in the electric system of the iontophoresis device. Iontophoresis is well classified for use in transdermal drug delivery. Unlike transdermal patches, this method relies on active transportation within an electric field. In the presence of an electric field electromigration and electroosmosis are the dominant forces in mass transport. These movements are measured in units of chemical flux.

A number of vitamins are negatively chargeable (hereinafter abbreviated as V) ($VB_2$, $VB_{12}$, VC, VE, folic acid, etc.). Some antibiotics are also negatively chargeable (penicillins water soluble drugs, chloramphenicol water soluble drugs).

Pharmaceutical Formulations

The present compositions can take the form of sustained-release formulations. In one embodiment, the pharmaceutically acceptable vehicle is a capsule (see e.g., U.S. Pat. No. 5,698,155). For example, in one embodiment, encapsulated vitamins are employed, including but not limited to encapsulated vitamin C available from Nanohybrid Co. (Seoul, Korea).

In a preferred embodiment, the active compound or compounds incorporated into the polymeric microfibers or nanofibers may be manipulated so as to form a solution of the active ingredient or ingredients in the nanofiber for controlled or sustained delivery of the active ingredient or ingredients. In some embodiments, said active ingredient or ingredients are activated upon wetting of the composition. Where necessary, the compositions can also include a solubilizing agent. Generally, the ingredients are mixed together in unit dosage form. In one embodiment, the unit dosage form is administered through an epicutaneously-applied composition.

Further, the effect of the active compound(s) can be delayed or prolonged by proper formulation. Compositions for use in accordance with the present invention can be formulated in conventional manner using one or more physiologically acceptable carriers or excipients. Thus, the compound and optionally another therapeutic or prophylactic agent and their physiologically acceptable salts and solvates can be formulated into pharmaceutical compositions for administration by topical or transdermal administration.

In certain preferred embodiments, the composition contains one or more unit dosage forms containing no more than the recommended dosage formulation as determined in the Physician's Desk Reference ($62^{nd}$ ed. 2008, herein incorporated by reference in its entirety).

Methods of administering the active compound and optionally another therapeutic or prophylactic agent are topical or transdermal. Administration can be local or systemic.

In specific embodiments, it can be desirable to administer the active compound locally to the area in need of treatment. This can be achieved, for example, and not by way of limitation, by local infusion topical application, e.g., in conjunction with a wound dressing after surgery. In one embodiment, the fiber matrices described herein can be applied to wounds as a film. Such matrices may include compounds that promote wound healing, such as propranolol or nitric oxide (which are useful to treat burns). In one embodiment, these compounds are encapsulated (e.g. in nanospheres which dissolve upon contact with an aqueous environment, including moist skin). Such matrices may include peptides that recruit cells to heal wounds, such as PHSRN as described in U.S. Pat. No. 6,025,150, hereby incorporated by reference. In another embodiment, laminin-111 peptides, A13 and C16, from the laminin alpha1 and gamma1 chain, respectively, are employed to promote wound healing. In some embodiments, it may be useful to apply non-dissolving or very slow dissolving films or patches so that the wound or burn is covered and protected for a desired time period.

The amount of the active compound that is effective in the treatment or prevention of skin diseases or disorders can be determined by standard research techniques. For example, the dosage of the active compound which will be effective in the treatment or prevention of a skin condition or disorder can be determined by administering the active compound to an animal in a model such as, e.g., the animal models known to those skilled in the art. In addition, in vitro assays can optionally be employed to help identify optimal dosage ranges.

Selection of a particular effective dose can be determined (e.g., via clinical trials) by a skilled artisan based upon the consideration of several factors, which will be known to one skilled in the art. Such factors include the disease to be treated or prevented, the symptoms involved, the subject's body mass, the subject's immune status and other factors known by the skilled artisan.

The dose of the active compound to be administered to a subject, such as a human, is rather widely variable and can be subject to independent judgment. It may be practical to administer the daily dose of the active compound at various hours of the day. However, in any given case, the amount of the active compound administered will depend on such factors as the solubility of the active component, the formulation used, and subject condition, for example, said subject's weight.

EXAMPLES

The following examples are provided in order to demonstrate and further illustrate certain preferred embodiments and aspects of the present invention and are not to be construed as limiting the scope thereof.

Example I

In a typical application, one selects an agent or agents for topical administration to a subject. In a preferred embodiment, said agent or agents are active ingredients that are targeted against a specific skin condition. In further embodiments, said agent or agents are a cosmetic. One or more dry active ingredients including but not limited to a cosmetic, peptide, vitamin, organic acid, oil or medicant are incorporated into a microfiber or nanofiber matrix via electrospinning. Further addition of the active ingredient or ingredients is achieved via intercalation of said active ingredient or ingredients into the void spaces of said microfiber or nanofiber matrix. A biopolymer including but in no way limited to collagen, cellulose or an algenate is impregnated with a solvent delivery system, i.e. a liquid. The solvated delivery biopolymer is then combined with the active ingredient-containing microfiber (or nanofiber) matrix to form one embodiment of the present invention.

Example II

In this example, a film or "patch" media is described based on a matrix having a hydrophilic fiber co-spun with a hydrophobic fiber. In this example, the hydrophilic polymer is either TECOGEL® 500 or TECOGEL® 2000. In this example, the hydrophobic polymer is either Carbothane 3575D or PolySulfone UDEL P3500NT (PolyCarbothane is available from Lubrizol, PolySulfone is available from Solvay). The hydrophilic fiber contains the chemistry (i.e. active ingredient) which will be eluted (or forced) out of the matrix when water is added (while not limited to any particular mechanism, it is believed that this is due to hydrophobic fibers inability to enlarge i.e. make additional volume in the matrix). The dosage delivered per unit time can be adjusted by proportionally changing the amount of hydrophilic versus hydrophobic polymer in this media. This patch media is developed under the name, Control Activity Manager, or CAM.

To fabricate the matrix, the hydrophilic and hydrophobic polymers are co-spun (electrospun as described above). More specifically, 4 mls of the PolySulfone solution (UDEL-P-3500+CHF+MEA) is co-spun with 20 ml "active" TG-2000 solution, (TG-2000+THF+MEA/Ethanol). The 20 ml "active" solution is a mix of:
1. 5 ml of TG-2000 solution.
2. 5 ml of TG-2000 solution+0.033 g low MW HA
3. 5 ml of TG-2000 solution+1.4 g GrantActive 168
4. 5 ml of TG-2000 solution+0.165 g Olive Oil The mix is done as follows: solutions 1+2+3 are added together to make a 15 mls solution; thereafter solution number 4 is added on top. Importantly, For solutions 1, 2 and 4, the TG solution is a mix of TecoGel 2000+THF+MEA. For solution number 3, the TG solution is a mix of: TecoGel 2000+THF+Ethanol (GrantActive 168 is water based so the MEA should be replaced by ethanol. The resulting media reacts with humid skin, it has a relatively slow dissolution rate.

Alternatively, active ingredients can be encapsulated in nanospheres, which can then be formulated into a CAM matrix by adding the nanospheres to the solution.

Example III

In this example, a film or "patch" media is described based on a matrix having only hydrophilic fibers produced from a fully water dissolvable polymer, such as PVP (Polyvinylpyrrolidone). This patch media is developed under the name, the Disappearing patch DISL.

To fabricate the matrix, the polymer is electrospun. The process parameters for nano electro spinning of the DISL patch are as follows:

| | |
|---|---|
| Distance from tip to collector: | 25 cm |
| Electric field at tip: | −20 KV |
| Electric field at collector: | +6 KV |
| Tip geometry: | 18 gauge |
| Flow rate: | 40 ml/h |
| Temperature: | +22 Celsius |
| Humidity: | 60% RH |

One example of a formulation of a DISL patch solution with an active ingredient (e.g. a stable form of vitamin C) along with additional (optional) ingredients includes:
Base 5 ml mixed of:
1. 25 g 11% PVP K90 solution (PVP K90+MEA+Ethanol)
2. 0.4 g VitaC hydrophobic (CNG G25)
3. 0.3 g HyaCare® 50 low MW Hyaluronic acid (while not limited to any particular mechanism, it is believed that HA because of its charge draws water into the structure)
4. 0.2 g Buthylene Glycol
Top 5 ml mixed of:
5. 25 g 11% PVP K90 solution (PVP K90+MEA+THF)
6. 3.8 g Olive Oil
7. 1.4 g Retinol Fluid [the pinacolyl ester of all-trans retinoic acid (tretinoin), available from Grant Industries, Inc.]
8. Fragrance Since Buthylene Glycol is water based, ethanol is used in the PVP K90 solution (see number 1, above). On the other hand, since Retinol Fluid is oil based, methanol is used in the PVP K90 solution (see number 5, above). This media instantly dissolves upon contact with moist skin and thereby delivers the active ingredients.

Alternatively, active ingredients can be encapsulated in nanospheres, which can then be formulated into a DISL matrix by adding the nanospheres to the solution.

Example IV

In this example, a film or "Biodegradable Dressing" media is described based on a matrix having three layers gradually changed from first hydrophilic layer incorporating Thrombin (such as RECOTHROM™ manufactured by Zymogenetic Inc or Tisseel a two component fibrin biomatrix manufactured by Baxter Inc) to a second hydrophobic layer creating a barrier preventing the Thrombin to migrate into third layer containing High molecular weight of Hyaluronic Acid. This patch media is developed as a combined Hemostate and anti-adhesion membrane.

To fabricate the matrix, three layers are electrospun from three different solutions via three tips on to one and same collector. The process begins by adding the first layer to the collector, then continuing with adding the first combined with second layer, then gradually removing the first layer while continuing with a second layer alone, then continuing with a combined second and third layer, then gradually removing the second layer and continuing with a third layer. Each layer originates from its specific solution spun by its dedicated tip. One example of formulation for a combined Hemostate and anti-adhesion membrane includes: First solution (5 g Poly-Active+24 g CHF+2 g Aceton+Thrombin was added to an amount of 47.5 IU/cm$^2$); Second solution (5 g PLA+24 g CHF+2 g MEA); Third solution (5 g PLA+24 g CHF+2 g MEA+0.1 g HA). The membrane showed haemostatic effect when applied to a blood oozing animal liver tissue and the HA eluted slowly giving a greasy surface.

Example V

In this example, one embodiment of an "on command" delivery approach is described. While nicotine is used in this example, the present invention contemplates "on command" with a variety of different active ingredients.

Nicotine "on command" delivery:

1) A sphere made by water dissolvable material like silica contains high concentration nicotine.

2) Those spheres containing nicotine are trapped within a "semi hydrophilic" matrix, originating from a solvent based solution.

3) The "sphere matrix" is placed as an ordinary nicotine plaster eluting a uniform dose through the skin over the day.

4) When the subject/patient feels a "sudden hunger for a smoke" he can wet the plaster (in whole or in part) in order to get a bolus dose on command.

Although the invention has been described with specific embodiments, it should be understood that the invention as claimed should not be unduly limited to such specific embodiments.

We claim:

1. A method for administering an active ingredient, comprising:
   a) providing:
      i) a subject, and
      ii) a single layer skin care composition comprising:
         1) an active ingredient selected from the group consisting of a cosmetic, peptide, vitamin, organic acid, oil or medicant, and
         2) electrospun polyvinylpyrrolidone polymeric fibers, said fibers forming an invisible film upon wetting that further dissolves upon further wetting; and
   b) administering said skin care composition to the skin of said subject; and
   c) wetting said skin care composition so as to make said composition invisible and to form an invisible film on said skin.

2. The method of claim 1, wherein said composition is administered topically.

3. The method of claim 1, wherein said subject exhibits symptoms associated with a skin disorder.

4. The method of claim 3, wherein said skin disorder is selected from the group consisting of acne, bed sores, rash, dry skin, dermal abrasions, dermatitis, sunburn, scars, hyperkeratosis, granuloma and skin ulceration.

5. The method of claim 1, wherein said vitamin is selected from the group consisting of vitamin C, vitamin A, vitamin E, vitamin K and vitamin B complex.

6. The method of claim 1, wherein said organic acid is hyaluronic acid.

7. The method of claim 1, wherein said composition lacks hydrophobic fibers.

8. The method of claim 1, wherein said active ingredient is a cosmetic.

9. The method of claim 8, wherein said cosmetic is botulinum toxin.

10. The method of claim 8, wherein said cosmetic is a dermal filler.

11. A method for administering a vitamin, comprising:
    a) providing:
    i) a subject, and
    ii) a single layer skin care composition comprising:
       1) a vitamin, and
       2) electrospun polyvinylpyrrolidone polymeric fibers;
    b) administering said skin care composition to the skin of said subject; and
    c) wetting said skin care composition so as to form an invisible film on said skin.

12. The method of claim 11, wherein said wetting comprises applying an aqueous solution.

13. The method of claim 11, wherein said vitamin is selected from the group consisting of vitamin C, vitamin A, vitamin E, vitamin K and vitamin B complex.

14. A method for administering an organic acid, comprising:
    a) providing:
    i) a subject, and
    ii) a single layer skin care composition comprising:
       1) an organic acid, and
       2) electrospun polyvinylpyrrolidone polymeric fibers;
    b) administering said skin care composition to the skin of said subject; and
    c) wetting said skin care composition so as to form an invisible film on said skin.

15. The method of claim 14, wherein said organic acid is hyaluronic acid.

16. The method of claim 15, wherein said hyaluronic acid is administered in combination with a medicant.

17. A method for administering a hormone, comprising:
    a) providing:
    i) a subject, and
    ii) a single layer skin care composition comprising:
       1) a hormone, and
       2) electrospun polyvinylpyrrolidone polymeric fibers;
    b) administering said skin care composition to the skin of said subject; and
    c) wetting said skin care composition so as to form an invisible film on said skin.

18. The method of claim 17, wherein said hormone is selected from the group consisting of androgens, estrogens and progestins, steroids and cortico steroids.

19. A method for administering an anti-inflammatory agent to a subject with a skin disorder, comprising:
    a) providing:
    i) a subject with a skin disorder, and
    ii) a single layer composition comprising:
       1) an anti-inflammatory agent, and
       2) electrospun polyvinylpyrrolidone polymeric fibers;
    b) administering said composition to the skin of said subject; and
    c) wetting said composition so as to form an invisible film on said skin.

20. The method of claim 19, wherein said skin disorder is selected from the group consisting of acne, bed sores, rash, dry skin, dermal abrasions, dermatitis, sunburn, scars, hyperkeratosis, granuloma and skin ulceration.

21. The method of claim 19, wherein said anti-inflammatory agent is diclofenac.

22. A method for administering a retinoid, comprising:
a) providing:
i) a subject, and
ii) a single layer skin care composition comprising:
1) a retinoid, and
2) electrospun polyvinylpyrrolidone polymeric fibers;
b) administering said skin care composition to the skin of said subject; and
c) wetting said skin care composition so as to form an invisible film on said skin.

23. The method of claim 22, wherein said subject has acne.

24. The method of claim 22, wherein said retinoid is tretinoin.

25. A method for administering an antibiotic, comprising:
a) providing:
i) a subject, and
ii) a single layer skin care composition comprising:
1) an antibiotic, and
2) electrospun polyvinylpyrrolidone polymeric fibers;
b) administering said skin care composition to the skin of said subject; and
c) wetting said skin care composition so as to form an invisible film on said skin.

26. The method of claim 1, further comprising wetting said invisible film so as to dissolve said film.

* * * * *